United States Patent [19]

Le et al.

[11] Patent Number: 5,177,284
[45] Date of Patent: Jan. 5, 1993

[54] CATALYSTS/PROCESS TO SYNTHESIZE ALKYLATED NAPHTHALENE SYNTHETIC FLUIDS WITH INCREASED ALPHA/BETA ISOMERS FOR IMPROVING PRODUCT QUALITIES

[75] Inventors: Quang N. Le, Cherry Hill; Joosup Shim, Wenonah, both of N.J.

[73] Assignee: Mobil Oil Corporation, Fairfax, Va.

[21] Appl. No.: 705,997

[22] Filed: May 28, 1991

[51] Int. Cl.$^5$ .............................................. C07C 2/66
[52] U.S. Cl. ..................................... 585/455; 585/467
[58] Field of Search ................................. 585/455, 467

[56] References Cited

U.S. PATENT DOCUMENTS

| | | | |
|---|---|---|---|
| 3,354,078 | 11/1967 | Miale et al. | 208/120 |
| 4,016,218 | 4/1977 | Haag et al. | 260/671 |
| 4,604,491 | 8/1986 | Dressler et al. | 585/26 |
| 4,714,794 | 12/1987 | Yoshida et al. | 585/26 |
| 4,861,932 | 8/1989 | Chen et al. | 585/412 |
| 4,876,408 | 10/1989 | Ratcliffe et al. | 585/467 |
| 4,954,325 | 9/1990 | Rubin et al. | 423/328 |
| 5,003,120 | 3/1991 | Newman et al. | 585/467 |
| 5,026,941 | 6/1991 | Oguri et al. | 585/467 |
| 5,026,942 | 6/1991 | Fellmann et al. | 585/467 |
| 5,030,785 | 7/1991 | Huss, Jr. et al. | 585/467 |
| 5,073,654 | 12/1991 | Arena et al. | 585/467 |

Primary Examiner—Asok Pal
Attorney, Agent, or Firm—Alexander J. McKillop; Charles J. Speciale; Howard M. Flournoy

[57] ABSTRACT

This application discloses critical parameters, including process conditions and catalysts which effect the alpha:beta ratio of alkylated naphthalene isomers. The use of low alkylation temperatures and of low acidity zeolite catalysts (e.g. steamed USY and zeolite beta) lead to an increase in the alpha:beta ratio. The alkylated naphthalene fluids with higher alpha:beta ratio exhibited significantly enhanced product qualities, including thermal and oxidative stabilities.

30 Claims, No Drawings

CATALYSTS/PROCESS TO SYNTHESIZE ALKYLATED NAPHTHALENE SYNTHETIC FLUIDS WITH INCREASED ALPHA/BETA ISOMERS FOR IMPROVING PRODUCT QUALITIES

CROSS-REFERENCE TO RELATED APPLICATIONS

This application is related to Serial No. 07/505,392 filed Apr. 6, 1990, entitled Naphthalene Alkylation Process and now pending and to Ser. No. 07/609,861, filed Jan. 11, 1991, entitled Lubricant Compositions and now pending.

BACKGROUND OF THE INVENTION

1. Field of the Invention

This application is directed to a process of synthesizing alkylated (aromatics) naphthalene synthetic fluids with increased alpha/beta isomers and improved product qualities.

2. Description of Related Art

Alkylated naphthalene is readily synthesized by alkylation of naphthalene with long chain alpha olefins (e.g., U.S. Pat. Nos. 4,604,491 and 4,714,794). Alkylation reaction occurs normally at alpha - (or 1-substitution) and beta - (or 2-substitution) positions of the naphthalene ring structure. U.S. Pat. No. 4,604,491 (1986, Koppers Company) disclosed that polyalkylated naphthalene mixture, produced from acid-treated clay, has preferentially the alpha:beta ratio ranging from 0.1 to 1.0. On the other hand, U.S. Pat. No. 4,714,794 (1987, Nippon Oil Company) disclosed the use of the same acid-treated clay catalyst to produce mono-alkylated naphthalenes with the alpha:beta ratio greater than 1.0. To our knowledge, the use of zeolite catalysts (e.g., USY and zeolite beta), the use of low acidity zeolites and/or the manipulation of processing conditions to enhance the formation of the desirable alpha-substitution are unique and novel.

BRIEF SUMMARY OF THE INVENTION

As disclosed in the above referred to patent applications which are incorporated herein by this reference, alkylated naphthalene synthetic fluids exhibit excellent product qualities, showing resistance to thermal and oxidation reactions. We have now found that an increase in the alpha/beta ratio (i.e. alkylation at alpha-position is preferred) enhances further the thermal and oxidative stabilities of alkylated naphthalene fluids. We have also discovered that there are several parameters effecting the alpha:beta ratio of alkylated naphthalene mixture:

Processing Conditions: Lowering the alkylation temperature increased the alpha:beta ratio.
Catalyst Structure: Zeolite beta and USY catalysts favor the formation of alpha-position.
Acid-treated clay catalyst forms mostly beta-position products.
Catalyst Acidity: Decreasing the zeolite acidity by steaming or cation-exchange increases the alpha:-beta ratio.

Accordingly, an object of the present invention is to provide a process for synthesizing alkylated aromatics, e.g., naphthalenes and substituted naphthalenes with increased alpha/beta isomers comprising selective manipulation of process parameters, catalyst structure and activity (or acidity).

DESCRIPTION OF THE PREFERRED EMBODIMENTS

The starting materials for the production of the alkylaromatic products include various aromatic compounds such as the low and high molecular weight alkylbenzenes, including low molecular weight alkylbenzenes such as toluene and the isomeric xylenes and mixtures of such materials. Higher molecular weight alkylbenzenes typically with a molecular weight of from about 300 to 3,000, may be alkylated in this way as well as other aromatics including anthracene, phenanthrene and aromatics with other fused ring systems. The process is, however, of primary applicability with the production of alkylated naphthalenes since these products have been found to provide lubricant materials of very good stability which may be blended with other lubricant components such as the poly-alphaolefins. For convenience and brevity, the process is described below primarily with reference to the production of alkylated naphthalenes but it may also be used in a similar manner for the production of other alkylated aromatics.

The starting materials for the production of alkylated naphthalenes include naphthalene itself as well the substituted naphthalenes which may contain one or more short chain alkyl groups containing up to about eight carbon atoms, such as methyl, ethyl or propyl. Suitable alkyl-substituted naphthalenes include alpha-methylnaphthalene, dimethylnaphthalene and ethylnaphthalene. Naphthalene itself is preferred since the resulting mono-alkylated products have better thermal and oxidative stability than the more highly alkylated materials for the reasons set out above.

The alkylating agents which are used to alkylate the naphthalene include any aliphatic or aromatic organic compound having one or more available alkylating aliphatic groups capable of alkylating the naphthalene. The alkylatable group itself should have at least about 6 carbon atoms, preferably at least about 8, and still more preferably at least about 12 carbon atoms. For the production of functional fluids and additives, the alkyl groups on the alkyl-naphthalene preferably have from about 12 to 30 carbon atoms, with particular preference to about 14 to 18 carbon atoms. A preferred class of alkylating agents are the olefins with the requisite number of carbon atoms, for example, the hexenes, heptenes, octenes, nonenes, decenes, undecenes, dodecenes. Mixtures of the olefins, e.g. mixtures of $C_{12}$–$C_{20}$ or $C_{14}$–$C_{18}$ olefins, are useful. Branched alkylating agents, especially oligomerized olefins such as the trimers, tetramers, pentamers, etc., of light olefins such as ethylene, propylene, the butylenes, etc., are also useful. Other useful alkylating agents which may be used, although less easily, include alcohols (inclusive of monoalcohols, dialcohols, trialcohols, etc.) such as hexanols, heptanols, octanols, nonanols, decanols, undecanols and dodecanols; and alkyl halides such as hexyl chlorides, octyl chlorides, dodecyl chlorides; and higher homologs.

The alkylation reaction between the naphthalene and the alkylating agent is carried out in the presence of a zeolite catalyst which contains a cation of certain specified radius. The molecular size of the alkylation products will require a relatively large pore size in the zeolite in order for the products to leave the zeolite, indicating the need for a relatively large pore size in the zeolite, which will also tent to reduce diffusion limitations with the long chain alkylating agents. The large pore size zeolites are the most useful zeolite catalysts for this purpose although the less highly constrained intermediate pore size zeolites may also be used, as discussed below. The large pore size zeolites are zeolites such as faujasite, the synthetic faujasites (zeolites X and Y), zeolite L, ZSM-4, ZSM-18, ZSM-20, mordenite and offretite which are generally useful for this purpose are characterized by the presence of a 12-membered oxygen ring system in the molecular structure and by the existence of pores with a minimum dimension of at least 7.4 Å, as described by Frilette et al. in *J. Catalysis* 67.218–222 (1981). See also Chen et al. Shape-Selective Catalysis in Industrial Applications, (Chemical industries; Vol. 36) Marcel Dekker Inc., New York 1989, ISBN 0-8247-7856-1 and Hoelderich et al. Angew. Chem. Int. Ed. Engl. 27 226–246 (1988), especially pp.226–229. The large pore size zeolites may also be characterized by a "Constraint Index" of not more than 2, in most cases not more than 1. Zeolite beta, a zeolite having a structure characterized by twelve-membered pore openings, is included in this class of zeolites although under certain circumstances it has a Constraint Index approaching the upper limit of 2 which is usually characteristic of this class of zeolites. The method for determining Constraint Index is described in U.S. Pat. No. 4,016,218, together with values for typical zeolites and of the significance of the Index in U.S. Pat. No.4,861,932. to which reference is made for a description of the test procedure and its interpretation.

Zeolites whose structure is that of a ten membered oxygen ring. generally regarded as the intermediate pore size zeolites may also be effective catalysts for this alkylation reaction if their structure is not too highly constrained. Thus, zeolites such as ZSM-12 (Constraint Index 2) may be effective catalysts for this reaction. The zeolite identified as MCM-22 is a particularly useful catalyst for this reaction because it gives a highly linear product with attachment to the alkyl chain at the 2-position. MCM-22 is described in U.S. Pat. No. 4,954,325, to which reference is made for a description of this zeolite. Thus, zeolites having a Constraint Index up to about 3 will generally be found to be useful catalysts, although the activity may be found to be dependent on the choice of alkylating agent, especially its chain length, a factor which imposes diffusion limitations upon the choice of zeolite.

The production of alkylnaphthalenes with alpha/beta ratios of 1 and higher by the use of Fiedel-Crafts or acid catalysts is disclosed by Yoshida et al., U.S. Pat. No. 4,714,794.

In general, the production of alkylnaphthalenes with alpha:beta ratios of 1 and higher is favored by the use of zeolite catalysts such as zeolite beta or zeolite Y preferably USY, of controlled acidity, preferably with an alpha value below about 200 and, for best results, below 100, e.g., about 25–50.

The alpha value of the zeolite is an approximate indication of the catalytic cracking activity of the catalyst compared to a standard catalyst. The alpha test gives the relative rate constant (rate of normal hexane conversion per volume of catalyst per unit time) of the test catalyst relative to the standard catalyst which is taken as an alpha of 1 (Rate Constant=0.016 sec $^{-1}$) The alpha test is described in U.S. Pat. No. 3,354,078 and in *J. Catalysis*, 4, 527 (1965); 6, 278 (1966); and 61, 395 (1980), to which reference is made for a description of the test. The experimental conditions of the test used to determine the alpha values referred to in this specification include a constant temperature of 538° C. and a variable flow rate as described in detail in *J. Catalysis*, 61, 395 (1980).

In general, lowering the alkylation temperature results in an increase in the alpha/beta ratio; the use of zeolite catalysts, especially zeolite beta and USY increases alpha over beta substitution; and decreasing zeolite acidity increases the alpha/beta ratio. More specifically we have found that highly suitable reaction (alkylation) temperatures in accordance with the invention may range from about 50° C. to about 300° C. and preferably from about 90° C. to about 200° C.; that the preferred alkylation catalysts are zeolites selected from zeolite beta and zeolite Y or USY; and that zeolite acidity as expressed by catalyst ALPHA may range from about 0.1 alpha to about 1000 alpha and preferably from about 1 alpha to about 100 alpha.

The zeolite may be composited with a matrix material or binder which is resistant to the temperatures and other conditions employed in the alkylation process. Such materials include active and inactive materials and synthetic or naturally occurring zeolites as well as inorganic materials such as clays, silica and/or metal oxides such as alumina, silica or silica-alumina. The latter may be either naturally occurring or in the form of gelatinous precipitates or gels including mixtures of silica and metal oxides. Use of an active material in conjunction with the zeolite may change the conversion and/or selectivity of the catalyst. Inactive materials suitably serve as diluents to control the amount of conversion so that alkylation products can be obtained economically and orderly without employing other means for controlling the rate of reaction. Binders which may be incorporated to improve the crush strength and other physically properties of the catalyst under commercial alkylation operating conditions include naturally occurring clays, e.g., bentonite and kaolin as well as the oxides referred to above.

The relative proportions of zeolite, present in finely divided crystalline form oxide matrix may vary widely, with the crystalline zeolite content ranging from about 1 to about 90 percent by weight and more usually, particularly when the composite is prepared in the form of beads, in the range of about 2 to about 80 weight percent of the composite.

Example A

This example illustrates the effect of alkylation temperature on the alpha:beta ratio. Mono-alkylated naphthalene fluids were prepared by alkylating naphthalene with alpha $C_{14}$ olefin (1:1.2 mole ratio) in an autoclave using a fresh hydrated USY catalyst (Catalyst A) at various reactor temperatures. Table 1 compares product properties and qualities as a function of reactor temperature:

TABLE 1

|  | Example 1 | Example 2 |
|---|---|---|
| RxR Temperature, °F. | 400 | 350 |
| Wt % Catalyst | 5 | 10 |
| AN Properties: |  |  |
| • Pour Point, °F. | <−65 | <−65 |
| KV @ 40° C., cSt | 23.85 | 22.00 |
| KV @ 100° C., cSt | 4.12 | 3.90 |
| Composition. wt % |  |  |
| Mono-Alkylated | 92 | 97 |
| Di-Alkylated | 8 | 3 |
| Alpha:Beta Ratio | 0.9 | 1.3 |
| AN Qualities* |  |  |

TABLE 1-continued

|  | Example 1 | Example 2 |
| --- | --- | --- |
| B-10, % Visc. Incr. | 4.7 | 2.1 |
| TAN | 0.87 | 0.49 |
| RBOT, min | 270 | 600+ |

*The B-10 catalytic oxidation test is described in U.S. Pat. Nos. 4,994,197 and 4,952,303. The RBOT is in accordance with ASTM D2272.

As shown, lowering the alkylation temperature from 400° to 350° F. leads to an increase in the alpha:beta ratio from 0.9 to 1.3, resulting in a significant improvement in AN product qualities. The alpha:beta ratio of mono-alkylated naphthalene was determined by the combination of high resolution GC/MS.

EXAMPLE B

This example illustrates the effect of zeolite structure on the alpha:beta ratio. Alkylated naphthalenes prepared from various zeolite catalysts including zeolite beta and USY using a similar procedure to that outlined in Example A (2:1 alpha $C_{14}=$:naphthalene mole ratio). For comparison purpose, a commercial acid-treated clay (Filtrol 13) was also used to synthesize the AN product. The AN properties are compared in Table 2:

TABLE 2

| Catalyst | Zeolite Beta | USY | Acid-Clay |
| --- | --- | --- | --- |
| Example | 3 | 4 | 5 |
| AN Properties |  |  |  |
| Pour Point, °F. | −55 | −40 | −45 |
| KV @ 40° C., cSt | 65.69 | 58.92 | 93.83 |
| KV @ 100° C., cSt | 8.79 | 8.54 | 11.02 |

Table 3 shows the alkylation isomer distribution of alkylated naphthalene products:

TABLE 3

| Substitution Position on | | | | |
| --- | --- | --- | --- | --- |
| Naphthalene | Alkyl Group | Beta | USY | Acid-Clay |
| B | 2 | 14 | 15 | 29 |
| A | 2 | 23 | 15 | 5 |
| B | 3 | 7 | 7 | 13 |
| A | 3 | 12 | 12 | 4 |
| B | 4 | 4 | 5 | 10 |
| B | 5 | 4 | 5 | 10 |
| A | 5 | 7 | 6 | 2 |
| A | 6 | 6 | 5 | 2 |
| A + B | 1 + 4 | 14 | 16 | 12 |
| B | 7 | 0 | 0 | 11 |
| A | 7 | 10 | 4 | 3 |
| Total Alpha:Beta Ratio | | 1.7 | 1.6 | 0.2 |

Results indicate that zeolite catalysts, especially zeolite beta and USY, promote the formation of alpha- over beta-substitution compared to an acid-treated clay catalyst.

EXAMPLE C

This example illustrates the effect of zeolite acidity on the formation of alpha- and beta-position isomers of AN products. Alkylated naphthalene fluids were prepared from zeolite beta at various acidity levels. Catalyst B is a fresh zeolite beta containing 35 wt% alumina binder, having an acidity of 220 alpha. The Catalyst B wa then steamed to reduce the acidity from 220 to 56 (Catalyst C) and finally to 36 alpha (Catalyst D). Alkylation reactions were carried out similar to that used in Example A using 2:1 molar ratio of alpha $C_{14}=$:naphthalene at 350° F. Table 4 compares AN properties and compositions:

TABLE 4

| Catalyst | B | C | D |
| --- | --- | --- | --- |
| Catalyst ALPHA | 220 | 56 | 36 |
| Example | 6 | 7 | 8 |
| AN Properties: |  |  |  |
| Pour Point, °F. | −50 | −55 | −55 |
| KV @ 40° C., cSt | 18.55 | 29.80 | 49.54 |
| KV @ 100° C., cSt | 3.90 | 5.21 | 7.26 |
| Alpha:Beta Ratio | 0.83 | 1.36 | 1.67 |

The results indicate that decreasing zeolite acidity by steaming increases significantly the alpha:beta ratio. The ratio increases two fold from 0.83 to 1:67 when zeolite beta acidity is reduced from 220 to 36 alpha.

In addition to zeolite beta, the positive effect of steaming on the alpha:beta ratio is also applicable to other zeolite catalyst systems, such as USY. Table 5 shows that a reduction in USY acidity by steaming leads to a significant increase in the alpha:ratio from about 1.3 to about 1.6:

TABLE 5

| Catalyst | Fresh USY | Steamed USY |
| --- | --- | --- |
| Example | 9 | 10 |
| AN Properties: |  |  |
| Pour Point, °F. | <−65 | −50 |
| KV @ 40° C., cSt | 22.92 | 50.47 |
| Alpha:Beta Ratio | 1.26 | 1.58 |

The alpha value is a measure of zeolite acidity. The acidity of the zeolite may be varied by conventional techniques including variation of the silica: alumina ratio, cation exchange or by selective poisoning. Accordingly, there are various methods of reducing zeolite acidity. Acidity can be reduced or eliminated by steaming, base exchange with alkali metal cations, etc. Steaming is but one of the options used. Other options also include alkali earth ion exchange with the aluminum acid sites and the use of as-synthesized boron-containing zeolite catalysts, including boron-zeolite beta. Boron-containing zeolites have very low alpha, typically in the range of less than 10, because the boron is synthesized in place of aluminum in the zeolite framework structure. For example, borosilicate zeolite beta has an alpha value of less than about 5. Other metallosilicates such as gallo or titanosilicate zeolite beta also have correspondingly low alpha values.

Alkylated naphthalene synthetic fluids as blending stocks with conventional PAO significantly enhance product qualities, including thermal/oxidative stability, solubility, elastomer compatibility and hydrolytic stability. Parameters, such as process conditions, catalyst structure and catalyst acidity, disclosed in the present application, will have a significant impact on the alpha:-beta ratio resulting in further product quality improvement of alkylated naphthalene synthetic lube basestocks.

We claim:

1. A process for preparing long chain alkyl-substituted aromatic compounds of increased alpha/beta ratio with respect to acid treated clay catalysts and steamed zeolite catalysts comprising reacting an aromatic compound with an alkylating agent possessing an alkylating aliphatic group having at least six carbon atoms under the following alkylation reaction conditions wherein the temperature varies from about 50° C. to about 300° C. under ambient or autogenous pressure in the presence of an alkylation catalyst comprising a porous crystalline zeolite having an alpha value of less than about 300 alpha to form an alkylated aromatic compound possessing at least one alkyl group derived from the alkylating agent.

2. The process according to claim 1 in which the alkylation temperature varies from about 90° C. to about 200° C.

3. The process according to claim 1 in which the zeolite has an alpha value ranging from about 5 alpha to about 250 alpha.

4. The process according to claim 1 in which the zeolite is selected from the group consisting of zeolite beta, zeolite Y and zeolite USY.

5. The process according to claim 4 in which the zeolite comprises zeolite beta.

6. The process according to claim 5 in which the zeolite is selected from a metallosilicate zeolite beta.

7. The process according to claim 6 in which the zeolite is selected from the group consisting of borosilicate, gallosilicate or titanosilicate zeolite beta.

8. The process according to claim 4 in which the zeolite comprises zeolite Y.

9. The process according to claim 4 in which the zeolite comprises zeolite USY.

10. The process according to claim 1 in which the alkylation agent is an alpha $C_{14}$ olefin, the alkylation temperature is from about 90° C. to about 200° C. and the zeolite is zeolite Y.

11. The process according to claim 1 in which the alkylation is carried out in the presence of zeolite USY.

12. The process according to claim 1 in which the alkylating aliphatic group contains from 8 to about 20 carbon atoms.

13. The process according to claim 1 in which the alkylating agent comprises an olefin.

14. The process according to claim 1 in which the aromatic compound comprises naphthalene or a substituted naphthalene.

15. The process according to claim 14 in which the aromatic compound comprises naphthalene.

16. A process for preparing long chain alkyl substituted naphthalenes which comprises reacting naphthalene with an olefin containing at least 8 carbon atoms as an alkylating agent under alkylation reaction conditions wherein the temperature varies from about 50° C. to about 300° C., the pressure is ambient or autogenous in the presence of an alkylation catalyst comprising a porous crystalline zeolite having an alpha value of less than about 300 alpha to form an alkylated naphthalene possessing at least one alkyl group derived from the alkylating agent.

17. The process according to claim 16 in which the zeolite is selected from the group consisting of zeolite beta, zeolite Y and zeolite USY.

18. The process according to claim 17 in which the zeolite comprises zeolite beta.

19. The process according to claim 18 in which the zeolite comprises a metallosilicate zeolite beta.

20. The process according to claim 19 in which the zeolite is selected from borosilicate, gallosilicate or titanosilicate zeolite beta.

21. The process according to claim 16 in which the alkylation agent is an alpha $C_{14}$ olefin, the temperature is 90° to about 200° C., the pressure is ambient or autogenous and the alkylation catalyst is zeolite Y.

22. The process according to claim 17 in which the zeolite is zeolite USY.

23. The process according to claim 16 in which the zeolite catalyst alpha value varies from less than 220 to about 5.

24. A process for preparing long chain alkyl substituted naphthalenes which comprises reacting naphthalene with a olefin containing from about 14 to about 20 carbon atoms as an alkylating agent under alkylation reaction conditions wherein the temperature varies from about 50° C. to about 300° C., the pressure is ambient or autogenous in the presence of an alkylation catalyst comprising a porous crystalline zeolite having an alpha value of less than about 300 to form an alkylated naphthalene possessing at least one alkyl group derived from the alkylating agent.

25. The process of claim 24 in which the zeolite is selected from the group consisting of zeolite beta, zeolite Y and zeolite USY.

26. The process according to claim 25 in which the zeolite comprises zeolite beta.

27. The process according to claim 26 in which the zeolite is selected from a metallosilicate zeolite beta.

28. The process according to claim 27 in which the zeolite is selected from the group consisting of borosilicate, gallosilicate or titanosilicate zeolite beta.

29. The process according to claim 25 in which the zeolite comprises zeolite Y.

30. The process according to claim 25 in which the zeolite comprises zeolite USY.

* * * * *